United States Patent
Yotsuya et al.

(10) Patent No.: US 6,653,333 B2
(45) Date of Patent: Nov. 25, 2003

(54) REMEDIES OR PREVENTIVES FOR DIGESTIVE DISEASES CONTAINING DIAMINOTRIFLUOROMETHYLPYRIDINE DERIVATIVES

(75) Inventors: Shuichi Yotsuya, Shiga (JP); Hirohiko Kimura, Shiga (JP); Tadao Bamba, Shiga (JP)

(73) Assignee: Ishihara Sangyo Kaisha, Ltd., Osaka (JP)

(*) Notice: Subject to any disclaimer, the term of this patent is extended or adjusted under 35 U.S.C. 154(b) by 0 days.

(21) Appl. No.: 10/182,374

(22) PCT Filed: Jan. 30, 2001

(86) PCT No.: PCT/JP01/00614
§ 371 (c)(1),
(2), (4) Date: Jul. 29, 2002

(87) PCT Pub. No.: WO01/26568
PCT Pub. Date: Aug. 9, 2001

(65) Prior Publication Data
US 2003/0027843 A1 Feb. 6, 2003

(30) Foreign Application Priority Data
Jan. 31, 2000 (JP) .......................................... 2000-22817

(51) Int. Cl.$^7$ ...................... A61K 31/44; C07D 213/02
(52) U.S. Cl. ..................................... 514/352; 546/308
(58) Field of Search ........................... 546/308; 514/352

(56) References Cited

U.S. PATENT DOCUMENTS

| 5,229,403 A | 7/1993 | Haga et al. ............... 514/352 |
| 6,197,796 B1 | 3/2001 | Ogura ......................... 514/352 |

FOREIGN PATENT DOCUMENTS

| JP | 7-126189 | 5/1995 |
| JP | 8-259447 | 10/1996 |
| JP | 9-12473 | 1/1997 |
| JP | 9-157182 | 6/1997 |
| JP | 10-101576 | 4/1998 |
| JP | 10-167985 | 6/1998 |
| JP | 10-330346 | 12/1998 |
| JP | 11-12171 | 1/1999 |
| JP | 11-92373 | 4/1999 |

OTHER PUBLICATIONS

H. Kimura, et al., Database Crossfire Beilstein Online!, Database Accession No. 7438760, 7440826, 7441843, 7442127, 7442736, 7442736, 7443382, pp. 1–59, XP 002234390, "Beilstein Institut Zur Fürderung Der Chemischen Wissenschaften", 2000 (English Abstracts of Chem. Pharm. Bull., vol. 43, No. 10, pp. 1696–1700, 1995).

J. Liang, et al., Chemical Abstracts, vol. 131, No. 2, p. 104, XP–002234386, "Novel Carboxamide Derivative (IS–741) Attenuates Lung Injury in Rats with Cerulein–Induced Pancreatitis Complicated by Endotoxemia", Dec. 7, 1999.

S. Yotsuya, et al., Chemical Abstracts, vol. 130, No. 26, p. 79, XP–002234387, "A Novel Synthetic Anti–Acute Pancreatitis Agent", Jun. 28, 1999.

J. Yamauchi, et al., Chemical Abstracts, vol. 130, No. 26, p. 79, XP–002234388, "A Novel Diamino–Pyridine Derivative Prevents Excessive Leukocyte Infilteration in Aggravation of Acute Necrotizing Pancreatitis", Jun. 28, 1999.

S. Isaji, et al., Chemical Abstracts, vol. 130, No. 26, p. 79, XP–002234389, "Effect of IS–741 (A New Synthetic Anti-inflammatory Agent) on Acute Necrotizing Pancreatitis in Dogs. Significance of its Inhibitory Effect on Cytosolic Phospholipase $A_2$", Jun. 28, 1999.

C. Bassi, Database Caplus Online !, Chemical Abstracts, 1 page, AN 2001–369260, XP–002234391, "IS–741 (Ishihara Sangyo)", 2000.

H. Takada, et al., Database Caplus Online !, Chemical Abstracts, 1 page, AN 2001–618828, XP–002234392, "IS–741; New Approach for the Management of Pancreatitis", 2000.

Japanese Pharmacology and Therapeutics, vol. 22, pp. 93–121 1994.

Mark H. Beers et al., eds. The Merck Manual, 17$^{th}$ Edition, p. 309 1999.

(List continued on next page.)

Primary Examiner—Zinna Northington Davis
(74) Attorney, Agent, or Firm—Oblon, Spivak, McClelland, Maier & Neustadt, P.C.

(57) ABSTRACT

A digestive system disease therapeutic or preventive agent containing as an active ingredient a diaminotrifluoromethylpyridine derivative represented by the formula (I) or its salt:

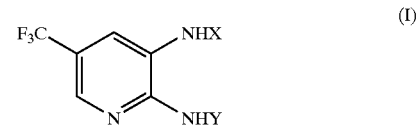

wherein X is a —CW$^1$R$^1$ group, a —COCOR$^2$ group, a —CW$^1$NHCOR$^2$ group, a —C(=W$^1$)W$^2$R$^3$ group or a —CW$^1$N(R$^4$)R$^5$ group; Y is an alkyl group, a —CW$^3$R$^6$ group, a —COCOR$^7$ group, a —NHCOR$^7$ group, a —C(=W$^3$)W$^4$R$^8$ group, a —(NH)$_m$SO$_2$R$^9$ group, a —(NH)$_m$SO$_2$OR$^{10}$ group or a —(NH)$_m$SO$_2$N(R$^{11}$)R$^{12}$ group; each of R$^1$, R$^6$ and R$^9$ is a chain hydrocarbon group, a monocyclic hydrocarbon group, a polycyclic hydrocarbon group, a monocyclic heterocycle group or a polycyclic heterocycle group; each of R$^2$ and R$^7$ is an-alkyl group, an alkoxy group, a phenyl group or a phenoxy group; each of R$^3$, R$^8$ and R$^{10}$ is an alkyl group, an alkenyl group, an alkynyl group, a cycloalkyl group, a phenyl group or a benzyl group; each of R$^4$, R$^5$, R$^{11}$ and R$^{12}$ is an alkyl group; each of W$^1$, W$^2$, W$^3$ and W$^4$ is an oxygen atom or a sulfur atom; and m is 0 or 1.

26 Claims, No Drawings

OTHER PUBLICATIONS

Enno Hentschel et al.: "Effect of ranitidine and amoxicillin plus metronidazole on the eradication of *helicobacter pylori* and the recurrence of duodenal ulcer" The New England Journal of Medicine, vol. 328, pp. 1725–1729 Feb. 04, 1993.

David Y. Graham et al.: "*Campylobacter pyloridis* gastritis: the past, the present and speculations about the future", The American Journal of Gastroenterology, vol. 82, No. 4, pp. 283–286 1987.

Willard J. Visek: "Ammonia: Its effects on biological systems, metabolic hormones, and reproduction" Journal of Dairy Science, vol. 67, pp. 481–498 1984.

Ulrich Klotz et al.: "Therapeutic efficacy of sulfasalazine and its metabolites in patients with ulcerative colitis and Crohn's Disease" The New England Journal of Medicine, vol. 303, No. 26, pp. 1499–1502 Dec. 25, 1980.

Hubert Allgayer: "Sulfasalazine and 5–ASA compounds" Gastrointestinal Pharamacology, vol. 21, No. 3, pp. 643–657 Sep. 1992.

Sogo Rinsho (Comprehensive Clinic) vol. 43, No. 9 1725–1729 1994.

T. Minami et al.: "Increased group II phospholipase A2 in colonic mucosa of patients with Crohn's disease and ulcerative colitis" GUT, vol. 35, pp. 1593–1598 1994.

I. Lilja et al.: "Phospholipase A2 gene expression and ctivity in histologically normal ileal mucosa and in Crohn's ileitis" GUT, vol. 37, pp. 380–385 1995.

J.W. Peterson et al.: "Phospholipase A2 activating protein and idiopathetic inflammatory bowel disease" GUT, vol. 39, pp. 698–704 1996.

REMEDIES OR PREVENTIVES FOR DIGESTIVE DISEASES CONTAINING DIAMINOTRIFLUOROMETHYLPYRIDINE DERIVATIVES

TECHNICAL FIELD

The present invention relates to a therapeutic or preventive agent containing as an active ingredient a diaminotrifluoromethylpyridine derivative or its salt, useful for digestive system diseases such as inflammatory bowel diseases, gastritis and peptic ulcer.

BACKGROUND ART

Japanese Patent No. 2762323 and U.S. Pat. No. 5,229,403 disclose that a diaminotrifluoromethylpyridine derivative or its salt has a phospholipase $A_2$ inhibitory action and is useful as an active ingredient of an anti-inflammatory agent or an anti-pancreatitis agent. They also disclose that (1) phospholipase $A_2$ is secreted or activated in platlets or inflammatory cells by stimulations and contributes to the production of a platlet activating factor (PAF) and arachidonic acid metabolites, (2) the arachidonic acid metabolites are closely related to various diseases, for example, inflammatory symptoms such as rheumatic arthritis, arthritis deformans, tendinitis, bursitis, psoriasis and related dermatitis; nasal and bronchial airway troubles such as allergic rhinitis and allergic bronchial asthma; and immediate hypersensitive reactions such as allergic conjunctivitis, (3) on the other hand, phospholipase $A_2$ secreted from pancreas is activated in the intestine and exhibits a digestive action, but once activated in the pancreas, it is believed to be one of the factors causing pancreatitis, and (4) the above diaminotrifluoromethylpyridine derivative inhibits phospholipase $A_2$ and thus is effective for treatment of diseases related to phospholipase $A_2$ such as inflammatory symptoms, nasal and bronchial airway troubles, immediate hypersensitive reactions or pancreatitis, and can be used as an anti-inflammatory agent, an agent for treating bronchial asthma, an anti-allergy agent, an anti-pancreatitis agent, an anti-nephritis agent or an anti-multiple organ failure agent.

Further, U.S. Pat. No. 5,492,908 discloses that such compounds can be used as a therapeutic agent for rheumatoid arthritis, and JP-A-10-298076 discloses that some of these compounds are effective as an anticancer agent having a carcinogenesis inhibitory effect.

Among digestive system diseases, diseases for which new therapeutic agents are particularly required, may, for example, be inflammatory bowel diseases, gastritis and peptic ulcer. The inflammatory bowel diseases are meant for enteritis developed at small intestine (including duodenum, jejunum and ileum) or large intestine (including cecum, colon and rectum), and they include enteritis, the causes of which are clear, such as infectious enteritis, ischemic enteritis, radioenteritis, drug enteritis and irritable bowel syndrome, intractable inflammatory bowel diseases, the causes of crises of which have not been clear yet, such as ulcerative colitis (nonspecific idiopathic colitis), Crohn's disease (regional enteritis), Crohn's disease of large bowel (granulomatous colitis or regional colitis) and entero-Behcet's disease, and further include enteritis, not only the causes of which have not been understood yet but also which themselves have not been specified.

Human ulcerative colitis is nonspecific idiopathic inflammatory bowel disease which forms erosion or ulcer on lamina propria mucosa or submucosa of large intestine mucosa from rectum to cecum, and it has conventionally been a relatively rare disease, however, the number of patients are rapidly increasing in recent years. As its clinical symptoms, characteristic pathognomonic findings such as diarrhea, bloody stool, abdominal pain and weight reduction may be mentioned, and it is an intractable disease with repetition of recurrence and remission. Its detailed cause and morbidity have not been clearly understood yet, but immunopathological mechanism and psychological factor are considered to be related. On the other hand, Crohn's disease is a disease wherein inflammation is formed not only on the mucosa but on entire bowel wall and non-diffusive and discontinuous lesion is formed on the entire digestive canal from the mouth cavity to the anus, and its detailed cause of disease has not been understood yet. During progress of the disease, in addition to denutrition, various serious digestive organ and parenteral symptoms such as intestinal stenosis, intestinal perforation, abdominal abscess and massive bleeding are likely to coincide, and the recurrence rate after operations is high with this disease.

As medical treatment for the ulcerative colitis, steroid hormone, Salazosulfapyridine (SASP) [Salazopyrin®, registered trademark] and metronidazole [Flagyl®, registered trademark] are mainly used [New England Journal of Medicine, vol. 25, p.1499 (1980), The Merck Manual, Seventeenth Edition, p.309, (1999)]. SASP used as the first choice drug particularly for active ulcerative colitis at a minor to moderate stage, which is an azo compound of 5-aminosalicylic acid (5-ASA) and sulfapyridine, is effective only when lesion is present in the large intestine, its effect is relatively weak at a severe stage, and it is in many cases used together with another agent such as a steroid drug even at a minor stage. Further, it is also pointed out that the effect is insufficient at an acute stage of inflammation. Its detailed mechanism of action is still unclear in many points even though its various actions have been reported such as prostaglandin synthesis inhibitory action, leukotriene synthesis inhibitory action, leukocyte chemotaxis inhibitory action, oxygen radical production inhibitory and erasing action, immunosuppressive action and anti-inflammatory action. Further, by taking the drug, adverse reactions such as liver function failure, nausea and vomiting, headache, pyrexia, hemolytic anemia, male sterility, abdominal dysphoria, rash, lymph node swelling, granulocytopenia and folic acid deficiency appear, and the frequency reaches 10 to 20% [Gastrointestinal Pharmacology, vol.21, p.643–658 (1992)]. With a purpose of decreasing such adverse reactions, mesalazine which is a sustained release preparation coated so that 5-ASA is formed by the pH in the intestine has been developed and used clinically, but the same problems as in the case of the above-described SASP have been reported, and its effect does not exceed SASP [Japanese Pharmacology & Therapeutics, vol.22, p.93–121 (1994)]. On the other hand, adrenocorticosteroids such as Predonine or Rinderon have commonly been used, however, on the other side of the therapeutic effect, other adverse reactions due to virus and bacterial infection or suppression of pituitary gland and adrenal cortex function have been pointed out as problems [Sogo Rinsho (Comprehensive Clinic), vol.43, p.1725–1729 (1994)], and because the prescription is very difficult, careful administration under hospitalization control is basically required. As therapeutic agents effective for Crohn's disease, SASP, 5-ASA, mercaptopurine, adrenocorticosteroid and metronidazole may, for example, be mentioned, but none of them is considered to have a sufficient clinical effect.

In recent years, for such inflammatory bowel diseases, new therapeutic agents such as a lipoxygenase inhibitor, a thromboxane $A_2$ receptor antagonist, a thromboxane $A_2$ synthetase inhibitor, an oxygen radical removing agent, an interleukin 1 (IL-1) antagonist (JP-A-9-157182) and a neutralizing antibody against tumor necrosis factor (TNF-α), and leukocytapheresis have been developed, however, development of more effective and safer therapeutic agents has been desired.

On the other hand, digestive ulcer such as gastric ulcer or duodenal ulcer exhibits various symptoms depending upon the location of the ulcer and the age of the patient, and the main cause has classically been considered as hypersecretion of gastric acid. As gastric acid hypersecretion inhibitors, $H_2$ blockers having a $H_2$ receptor antagonistic action (such as cimetidine, ranitidine, famotidine, roxatidine acetate and nizatidine) and proton pump inhibitors (PPI: such as omeprazole and lansoprazole) have been used clinically. No one disputes that the cure rate of gastric ulcer and duodenal ulcer was remarkably improved by appearance of these drugs, and these drugs are mainly used for the treatment against digestive ulcer at present. However, many clinical cases have been reported that even though the ulcer is temporarily cured by such a drug, the ulcer recrudesces with a high ratio so long as *Helicobacter pylori* is present in the digestive canal [New England Journal of Medicine, vol.328, p.308 (1993)] as described hereinafter. Further, the incidence of digestive ulcer due to application of a nonsteroidal anti-inflammatory agent tends to be high with patients who take an $H_2$ blocker or PPI for a long period of time, such being problematic.

In recent years, it has been clarified that *Helicobacter pylori* is an important pathogenic factor in crisis of gastritis, gastric ulcer, duodenal ulcer and stomach cancer [American Journal of Gastroenterology, vol.82, p.2283 (1987)], and a treatment with an antibacterial agent in addition to a gastric acid secretion inhibitor has been applied to *Helicobacter pylori* positive digestive ulcer cases regardless of whether it is initial crisis or recurrent crisis. There are various opinions with regard to the action of *Helicobacter pylori*, and according to one theory, it has been reported that urease produced by *Helicobacter pylori* under an acidic condition decomposes urea present in the stomach to produce ammonia, and the produced ammonia directly impairs the gastric mucosa [Journal of Dairy Science, vol.67, p.481 (1984)]. As bacterial elimination treatment against *Helicobacter pylori*, various treatment methods employing mainly a bismuth preparation, an antibacterial agent or an antiprotozoan agent have been devised, however, no sufficient bacterial elimination effect can be obtained by single use of these drugs, and the treatment is carried out mainly by multiple drug combination. For example, in Europe and U.S., classical three-drug combination treatment with bismuth, metronidazole and tetracycline has been carried out, and a bacterial elimination ratio of at least 90% can be obtained, however, appearance of adverse reactions with high frequency and complicated method of application lead to poor compliance, and such a treatment is not widely used in Japan. Further, two drug combination treatment by PPI and an antibacterial agent such as amoxicillin or clarithromycin, or a short-term three drug combination treatment wherein omeprazole, clarithromycin and nitroimidazole in usual dosage are used together for one weak, have been developed. However, many cases where no stable bacterial elimination ratio can be obtained or cases where recurrence takes place due to appearance of resistant bacterium, have been reported. Further, as application of an antibacterial agent in a large amount is required, it is hard for patients to take the agent, and it is known that adverse reactions such as diarrhea, nausea and vomiting occur in many cases, and such is generally known as a problem to be overcome.

Gastritis caused by impairment of the gastric mucosa are roughly classified into acute erosive gastritis, chronic erosive gastritis and nonerosive gastritis, postgastrectomy gastritis and other gastritis syndrome. The causes are various but many of them are in common with the cases of the above-described digestive ulcer, and the mainstream of the treatment method at present is single or combination use of $H_2$ blockers, proton pump inhibitors and *Helicobacter pylori* elimination agents. From recent studies, it has been reported that as novel therapeutic agents for digestive ulcer or gastritis, a digestive canal mucosa adherent anti-helicobacter pylori agent containing an antibacterial substance and an antiulcer substance (JP-A-7-126189, JP-A-10-167985), a cholecystokinin antagonist (JP-A-8-259447), a mucin production accelerator containing lactoferrin as an active ingredient (JP-A-9-12473), an aminoalkylpyridyloxy derivative having both $H_2$ receptor antagonistic action and gastric mucosa protective action (JP-A-11-92373), etc., are useful.

Further, JP-A-11-12171, JP-A-10-330346 and JP-A-10-101576 disclose that a 1,4-benzodioxin derivative having a selective $\beta_3$ receptor agonistic action, a straight chain nitron derivative having a free radical scavenging action and a drug containing Gricetin and glutamine (or a glutamine derivative) as active ingredients, respectively, are useful for treatment of various digestive system diseases, however, development of safer drugs having more excellent therapeutic effects has been desired.

DISCLOSURE OF THE INVENTION

The present inventors have conducted extensive studies on pharmacological effects of diaminotrifluoromethylpyridine derivatives or their salts and as a result, found that these compounds have excellent therapeutic effects on digestive system diseases such as inflammatory bowel disease, gastritis and peptic ulcer, and the present invention has been accomplished on the basis of this discovery.

The present invention provides a therapeutic or preventive agent for digestive system diseases, containing as an active ingredient a diaminotrifluoromethylpyridine derivative represented by the formula (I) or its salt:

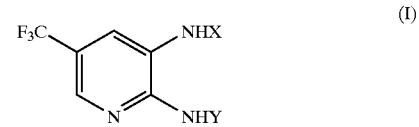

(I)

wherein X is a —$CW^1R^1$ group, a —$COCOR^2$ group, a —$CW^1NHCOR^2$ group, a —$C(=W^1)W^2R^3$ group or a —$CW^1N(R^4)R^5$ group; Y is an alkyl group, a —$CW^3R^6$ group, a —$COCOR^7$ group, a —$NHCOR^7$ group, a —$C(=W^3)W^4R^8$ group, a —$(NH)_mSO_2R^9$ group, a —$(NH)_mSO_2OR^{10}$ group or a —$(NH)_mSO_2N(R^{11})R^{12}$ group; each of $R^1$, $R^6$ and $R^9$ which are independent of one another, is a chain hydrocarbon group which may be substituted, a monocyclic hydrocarbon group which may be substituted, a polycyclic hydrocarbon group which may be substituted, a monocyclic heterocycle group which may be substituted or a polycyclic heterocycle group which may be substituted; each of $R^2$ and $R^7$ which are independent of each other, is an alkyl group which may be substituted, an alkoxy group which may be substituted, a phenyl group which may be substituted or a phenoxy group which may be substituted; each of $R^3$, $R^8$ and $R^{10}$ which are independent of one another, is an alkyl group which may be substituted, an alkenyl group which may be substituted, an alkynyl group which may be substituted, a cycloalkyl group which may be substituted, a phenyl group which may be substituted or a benzyl group which may be substituted; each of $R^4$, $R^5$, $R^{11}$ and $R^{12}$ which are independent of one another, is an alkyl group which may be substituted; each of $W^1$, $W^2$, $W^3$ and $W^4$ which are independent of one another, is an oxygen atom or a sulfur atom; and m is 0 or 1, excluding a case where one of X and Y is a —$COCF_2X^1$ group (wherein $X^1$ is a hydrogen atom, a halogen atom, an alkyl group or a haloalkyl group), and the other is a —$COCF_2X^2$ group (wherein $X^2$ is a hydrogen atom, a halogen atom, an alkyl group, a haloalkyl group or an alkylcarbonyl group), a —$COOX^3$ group (wherein $X^3$ is an alkyl group which may be substituted or a phenyl group which may be substituted) or a —$COX^4$ group (wherein $X^4$ is an alkyl group, a haloalkyl group, an alkenyl group, an alkynyl group, a phenyl group which may be substituted, a furanyl group or a naphthyl group).

In the above formula (I), the above chain hydrocarbon group for each of $R^1$, $R^6$ and $R^9$ may, for example, be an alkyl group, an alkenyl group or an alkynyl group. The above monocyclic hydrocarbon group may be a cycloalkyl group, a cycloalkenyl group or a phenyl group. The polycyclic hydrocarbon group may, for example, be a condensed polycyclic hydrocarbon group such as a naphthyl group, a tetrahydronaphthyl group or an indanyl group, or a bridged polycyclic hydrocarbon group such as an adamantyl group, a noradamantyl group, a norbornanyl group or a norbornanonyl group, and the above monocyclic heterocycle group may, for example, be a pyrrolyl group, a furanyl group, a thienyl group, a pyrazolyl group, an imidazolyl group, an oxazolyl group, an isoxazolyl group, a thiazolyl group, an isothiazolyl group, a thiadiazolyl group, a pyrrolinyl group, a pyrrolidinyl group, a dihydrofuranyl group, a tetrahydrofuranyl group, a dihydrothienyl group, a tetrahydrothienyl group, a pyrazolinyl group, a hydantoinyl group, an oxazolinyl group, an isoxazolinyl group, an isoxazolidinyl group, a thiazolinyl group, a thiazolidinyl group, a dioxolanyl group, a dithiolanyl group, a pyridyl group, a pyridazinyl group, a pyrimidinyl group, a pyrazinyl group, a dihydropyridyl group, a tetrahydropyridyl group, a piperidinyl group, a dihydrooxopyridazinyl group, a tetrahydrooxopyridazinyl group, a dihydrooxopyrimidinyl group, a tetrahydrooxopyrimidinyl group, a piperazinyl group, a dihydropyranyl group, a tetrahydropyranyl group, a dioxanyl group, a dihydrodithinyl group, a dithianyl group or a morphorinyl group. The above polycyclic heterocycle group may be a condensed polycyclic heterocycle group such as a thienothienyl group, a dihydrocyclopentathienyl group, an indolyl group, a benzofuranyl group, a benzothienyl group, a benzoxazolyl group, a benzisoxazolyl group, a benzothiazolyl group, a benzimidazolyl group, a tetrahydrobenzothienyl group, a dihydrobenzofuranyl group, a tetrahydrobenzisoxazolyl group, a benzodioxolyl group, a quinolinyl group, an isoquinolinyl group, a benzodioxanyl group or a quinoxalinyl group, or a bridged polycyclic heterocycle group such as a quinuclidinyl group.

The substituent for each of the chain hydrocarbon group which may be substituted for each of $R^1$, $R^6$ and $R^9$, the alkyl group which may be substituted and the alkoxy group which may be substituted for each of $R^2$ and $R^7$, the alkyl group which may be substituted, the alkenyl group which may be substituted and the alkynyl group which may be substituted for each of $R^3$, $R^8$ and $R^{10}$, the alkyl group which may be substituted for each of $R^4$, $R^5$, $R^{11}$ and $R^{12}$, and the alkyl group which may be substituted for $X^3$, may, for example, be a halogen atom, an alkoxy group, a haloalkoxy group, an alkylthio group, a cycloalkyl group, a cycloalkoxy group, a cycloalkenyl group, a cycloalkenyloxy group, an alkoxycarbonyl group, an alkylcarbonyl group, an alkylcarbonyloxy group, an aryl group, an aryloxy group, an arylthio group, an amino group or an amino group substituted with an alkyl group. The number of such substituents or substituents on such substituents may be one or more, and when the number is two or more, such substituents may be the same or different.

Further, the substituent for each of the monocyclic hydrocarbon group which may be substituted, the polycyclic hydrocarbon group which may be substituted, the monocyclic heterocycle group which may be substituted and the polycyclic heterocycle group which may be substituted for each of $R^1$, $R^6$ and $R^9$, the phenyl group which may be substituted and the phenoxy group which may be substituted for each of $R^2$ and $R^7$, the cycloalkyl group which may be substituted, the phenyl group which may be substituted and the benzyl group which may be substituted for each of $R^3$, $R^8$ and $R^{10}$, and the phenyl group which may be substituted for $X^3$, may, for example, be a halogen atom, an alkyl group, a haloalkyl group, an alkoxy group, a haloalkoxy group, an alkylthio group, a cycloalkyl group, a cycloalkoxy group, a cycloalkenyl group, a cycloalkenyloxy group, an alkoxycarbonyl group, an alkylcarbonyl group, an alkylcarbonyloxy group, an aryl group, an aryloxy group, an arylthio group, an amino group, an amino group substituted with an alkyl group, a cyano group or a nitro group. The number of such substituents or substituents on such substituents may be one or more, and when the number is two or more, such substituents may be the same or different.

In the formula (I), the alkyl group and the alkyl moiety contained in each of X and Y may, for example, be $C_{1-18}$ alkyl such as a methyl group, an ethyl group, a propyl group, a butyl group, a pentyl group, a hexyl group, a heptyl group, an octyl group, a decyl group or a nonadecyl group, and they include linear or branched aliphatic structural isomers. The alkenyl group and the alkenyl moiety contained in each of X and Y may be $C_{2-18}$ alkenyl such as a vinyl group, a propenyl group, a butenyl group, a pentenyl group, a hexenyl group, a decenyl group or a nonadecenyl group, and they include linear or branched aliphatic structural isomers. The alkynyl group and the alkynyl moiety contained in each of X and Y may be $C_{2-18}$ alkynyl such as an ethynyl group, a propynyl group, a butynyl group, a pentynyl group, a hexynyl group, a decynyl group or a nonadecynyl group, and they include linear or branched aliphatic structural isomers. The cycloalkyl group and the cycloalkyl moiety contained in each of X and Y may be $C_{3-8}$ cycloalkyl such as a cyclopropyl group, a cyclobutyl group, a cyclopentyl group, a cyclohexyl group or a cyclooctyl group. The cycloalkenyl group and the cycloalkenylmoiety contained in each of X and Y may be $C_{5-8}$ cycloalkenyl such as a cyclopentenyl group, a cyclohexenyl group or a cyclooctenyl group. Further, the halogen atom contained in each of X and Y may be a fluorine atom, a chlorine atom, a bromine atom or an iodine atom. The aryl group and the aryl moiety contained in each of X and Y may, for example, be a phenyl group, a thienyl group, a furanyl group, a pyridyl group, a naphthyl group, a benzothienyl group, a benzofuranyl group or a quinolinyl group.

Now, preferred embodiments of the compounds of the present invention will be described. In the formula (I), it is preferred that X is a —$CW^1R^1$ group or a —$C(=W^1)W^2R^3$ group and Y is a —$SO_2R^9$ group. Each of $R^1$ and $R^6$ is preferably an alkyl group which may be substituted, an alkenyl group which may be substituted, a cycloalkyl group which may be substituted, a cycloalkenyl group which may be substituted, a phenyl group which may be substituted, a tetrahydronaphthyl group which may be substituted, an indanyl group which may be substituted, a furanyl group which may be substituted or a thienyl group which may be substituted; more preferably an alkyl group, a haloalkyl group, an alkoxycarbonylalkyl group, an alkenyl group, a haloalkenyl group, a cycloalkyl group, a cycloalkyl group substituted with a halogen atom, a phenyl group, a phenyl group substituted with a halogen atom, a phenyl group substituted with an alkyl group or a haloalkyl group, a phenyl group substituted with an alkoxy group or a haloalkoxy group, a tetrahydronaphthyl group, an indanyl group, a furanyl group or a thienyl group. Each of $R^2$ and $R^7$ is preferably an alkoxy group which may be substituted or a phenyl group which may be substituted; more preferably an alkoxy group, a haloalkoxy group, a phenyl group or a phenyl group substituted with a halogen atom. Each of $R^3$, $R^8$ and $R^{10}$ is preferably an alkyl group which may be substituted; more preferably an alkyl group or a haloalkyl group. Each of $R^4$, $R^5$, $R^{11}$ and $R^{12}$ is preferably an alkyl group. $R^9$ is preferably an alkyl group which may be substituted, an alkenyl group which may be substituted, a cycloalkyl group which may be substituted, a cycloalkenyl group which may be substituted or a phenyl group which may be substituted; more preferably an alkyl group, a haloalkyl group, a phenyl group, a phenyl group substituted with a halogen atom, a phenyl group substituted with an alkyl group or a haloalkyl group or a phenyl group substituted with an alkoxy group or a haloalkoxy group.

Preferred compounds among the compounds of the present invention are compounds of the above formula (I) wherein X is an alkoxycarbonylalkylcarbonyl group, an alkenylcarbonyl group, an alkenylcarbonyl group substituted with a thienyl group, a cycloalkylcarbonyl group, an indanylcarbonyl group, a furancarbonyl group, a thiophenecarbonyl group, a tetrahydronaphthylcarbonyl group or a benzoyl group which may be substituted with a halogen atom or a haloalkyl group, and Y is an alkylsulfonyl group. Specific compounds include N-(2-methylsulfonylamino-5-trifluoromethyl-3-pyridyl)-4-fluorobenzamide, N-(2-isopropylsulfonylamino-5-trifluoromethyl-3-pyridyl)-3-fluorobenzamide, N-(2-methylsulfonylamino-5-trifluoromethyl-3-pyridyl)-2-furancarboxamide, N-(2-isopropylsulfonylamino-5-trifluoromethyl-3-pyridyl) cyclopentanecarboxamide, N-(2-ethylsulfonylamino-5-trifluoromethyl-3-pyridyl)cyclohexanecarboxamide, N-(2-methylsulfonylamino-5-trifluoromethyl-3-pyridyl)-5-indanecarboxamide, N-(2-methylsulfonylamino-5-trifluoromethyl-3-pyridyl)acetoxyacetamide, N-(2-methylsulfonylamino-5-trifluoromethyl-3-pyridyl) crotonamide, N-(2-methylsulfonylamino-5-trifluoromethyl-3-pyridyl)-2-thiophenecarboxamide, N-(2-methylsulfonylamino-5-trifluoromethyl-3-pyridyl)-3-trifluoromethylbenzamide, N-(2-ethylsulfonylamino-5-trifluoromethyl-3-pyridyl)-3-fluorobenzamide, N-(2-methylsulfonylamino-5-trifluoromethyl-3-pyridyl)-6-(1,2,3,4-tetrahydronaphthalene)carboxamide, N-(2-ethylsulfonylamino-5-trifluoromethyl-3-pyridyl)crotonamide, N-(2-methylsulfonylamino-5-trifluoromethyl-3-pyridyl)-3-(2-thienyl)acrylamide, and their salts.

More preferred compounds may be compounds of the above formula (I) wherein X is a cycloalkylcarbonyl group, a furancarbonyl group or a benzoyl group which may be substituted with halogen, and Y is an alkylsulfonyl group. Specific compounds include N-(2-ethylsulfonylamino-5-trifluoromethyl-3-pyridyl)cyclohexanecarboxamide, N-(2-methylsulfonylamino-5-trifluoromethyl-3-pyridyl)-4-fluorobenzamide, N-(2-isopropylsulfonylamino-5-trifluoromethyl-3-pyridyl)-3-fluorobenzamide, N-(2-methylsulfonylamino-5-trifluoromethyl-3-pyridyl)-2-furancarboxamide and N-(2-isopropylsulfonylamino-5-trifluoromethyl-3-pyridyl)cyclopentanecarboxamide, and their salts.

The compounds represented by the formula (I) may form a salt when Y is —$SO_2R^9$ group (wherein $R^9$ is as defined above). Such a salt may be any pharmaceutically acceptable salt, for example, an alkali metal salt such as a potassium salt or a sodium salt, an alkaline earth metal salt such as a calcium salt, or an organic amine salt such as a triethanolamine salt or a tris(hydroxymethyl)aminomethane salt. Such a salt may have crystal water.

The compounds represented by the formula (I) can be prepared, for example, by a process as disclosed in Japanese Patent No. 2762323. Further, these compounds have geometrical isomers depending upon the type of their substituents, and the present invention include isomers (cis-forms and trans-forms) and isomer mixtures.

The compounds of the present invention represented by the above formula (I) are useful as an active ingredient for a therapeutic or preventive agent for digestive system diseases. Particularly, they are useful as an active ingredient for a therapeutic or preventive agent for inflammatory bowel diseases such as ulcerative colitis (nonspecific idiopathic colitis), Crohn's disease (regional enteritis), large intestine Crohn's disease (granulomatous colitis or regional colitis), entero-Behcet's disease, infectious enteritis, ischemic enteritis, radioenteritis, drug enteritis and irritable bowel syndrome, digestive ulcer such as gastric ulcer and duodenal ulcer, and gastritis. They are particularly useful as an active ingredient for a therapeutic or preventive agent for the above ulcerative colitis, Crohn's disease, large intestine Crohn's disease and entero-Behcet's disease, and they are preferably used as an active ingredient for a therapeutic or preventive agent for ulcerative colitis and Crohn's disease. Further, they are expected to be more effective by combination with another drug such as Chinese herbal remedy.

To administer the compound of the present invention as an active ingredient for a therapeutic drug for digestive system diseases such as ulcerative colitis, Crohn's disease, gastric ulcer, duodenal ulcer and gastritis, it is formulated alone or together with a pharmaceutically acceptable carrier into a drug composition suitable for peroral or parenteral administration, such as a tablet, a powder, a capsule, a granule, an injection drug, an ointment, an inhalant, an enema or a suppository, and it is administered in the form of such a drug formulation. Further, in recent years, a drug formulation comprising a suppository base and a digestive canal mucosa adhesive matrix for peroral administration incorporated into the base, the matrix being capable of prolonging the retention time in the digestive canal to make the active ingredient for a drug for gastric, duodenal, large intestine, small intestine or rectal ulcer affect over a long period of time at a high concentration with a high efficiency, utilizing adhesive property to the gastric mucosa or intestinal canal mucosa, has been reported (JP-A-5-132416, JP-A-7-330582), and administration employing it is also possible.

As a drug formulation suitable for peroral administration, a solid composition such as a tablet, a capsule, a powder, a granule or a troach; or a liquid composition such as a syrup suspension, may, for example, be mentioned. The solid composition such as a tablet, a capsule, a powder, a granule or a troach may contain a binder such as fine crystalline cellulose, gum arabic, tragacanth gum, gelatine or polyvinyl pyrrolidone; an excipient such as starch, lactose or carboxymethyl cellulose; a disintegrator such as arginic acid, corn starch or carboxymethyl cellulose; a lubricant such as magnesium stearate, light silicic anhydride or colloidal silicon dioxide; a sweetener such as sucrose; or a flavoring agent such as peppermint or methyl salicylate. The liquid composition such as a syrup or a suspension may contain sorbitol, gelatine, methyl cellulose, carboxymethyl cellulose, a vegetable oil such as a peanut oil, an emulsifier such as lecithin as well as a sweetener, a preservative, a colorant or a flavoring agent, as the case requires. Such a composition may be provided in the form of a dried formulation. These formulations preferably contain from 1 to 95 wt % of the active ingredient compound.

A drug formulation suitable for parenteral administration may, for example, be an injection drug. The injection drug may be prepared by dissolving the compound in the form of a salt in usual water for injection, or may be formulated into a formulation suitable for injection such as a suspension or an emulsion (in a mixture with a medically acceptable oil or liquid). In such a case, it may contain benzyl alcohol as an antibacterial agent, ascorbic acid as an antioxidant, a medically acceptable buffer solution or a reagent for adjusting the osmotic pressure. Such an injection drug preferably contains from 0.1 to 8 wt % of the active ingredient compound.

A drug formulation suitable for topical or per rectal administration may, for example, be an inhalant, an ointment, an enema or a suppository. The inhalant may be formulated by dissolving the compound of the present invention alone or together with a medically acceptable inert carrier in an aerosol or nebulizer solution, or may be administered to the respiratory airway in the form of fine powder for inhalation. In the case of fine powder for inhalation, the particle size is usually not more than $50\mu$, preferably not more than $10\mu$. Such an inhalant may be used, if necessary, in combination with other antiasthematic agent or bronchodilator.

An ointment may be prepared by a conventional method by an addition of e.g. a commonly employed base. The ointment preferably contains from 0.1 to 30 wt % of the active ingredient compound.

The suppository may contain a carrier for formulation which is well known in this field, such as polyethylene glycol, lanolin, cacao butter or fatty acid triglyceride. The suppository preferably contains from 0.1 to 95 wt % of the active ingredient compound.

The above drug compositions suitable for peroral, parenteral, topical or per rectal administration, may be formulated by known methods so that after administration to a patient, the active ingredient will be rapidly discharged, gradually discharged or belatedly discharged.

Needless to say, the dose of the compound of the present invention varies depending upon the type of the compound, the administration method, the condition of the patient or the animal to be treated, and the optimum dose and the number of administration under a specific condition must be determined by the judgment of a competent doctor. Usually, however, a daily dose to an adult is from about 0.1 mg to about 10 g, preferably from about 1 mg to about 1 g. In the case of the above inhalation method, the dose of the compound of the present invention is preferably from about 0.01 mg to about 1 g per administration.

Now, specific Formulation Examples of the therapeutic or preventive agent of the present invention will be given. However, the formulation of the present invention is not limited thereto.

FORMULATION EXAMPLE 1 (Tablet)

| | |
|---|---|
| (1) Active ingredient | 20 mg |
| (2) Lactose | 150 mg |
| (3) Starch | 30 mg |
| (4) Magnesium stearate | 6 mg |

The above composition is tabletted so that the components (1) to (4) constitute one tablet.

FORMULATION EXAMPLE 2)Powder, Subtilized Granule or Granule)

| | | |
|---|---|---|
| (1) | Active ingredient | 20 mg |
| (2) | Sugar ester (DK ester F-160, tradename, manufactured by DAI-ICHI KOGYO SEIYAKU CO., LTD.) | 180 mg |
| (3) | Surfactant (Dekagreen 1-L, tradename, manufactured by Nikko Chemicals Co., Ltd.) | 15 mg |
| (4) | Light silicic anhydride | 25 mg |

The above components (1) to (4) are mixed and formed into a powder, or subtilized granule or granule by granulation. Such a powder, subtilized granule or granule may be sealed in a capsule to obtain a capsule drug.

FORMULATION EXAMPLE 3 (Hard Gelatine Capsule Drug)

| | |
|---|---|
| (1) Active ingredient | 25 mg |
| (2) Starch | 200 mg |
| (3) Magnesium stearate | 10 mg |

The above components (1) to (3) are packed in one hard gelatine capsule to obtain a hard gelatine capsule drug.

FORMULATION EXAMPLE 4 (Injection Drug)

| | |
|---|---|
| (1) Active ingredient | 1 mg |
| (2) Glucose | 10 mg |
| (3) tris(hydroxymethyl)aminomethane | 2.16 mg |

A tris buffer containing the components (1) to (3) is freeze-dried to prepare an injection drug.

FORMULATION EXAMPLE 5 (Ointment for External Skin Application)

| | |
|---|---|
| (1) Active ingredient | 0.5 g |
| (2) White vaseline | 25 g |
| (3) Stearyl alcohol | 22 g |
| (4) Propylene glycol | 12 g |
| (5) Sodium lauryl sulfate | 1.5 g |
| (6) Ethyl parahydroxybenzoate | 0.025 g |
| (7) Propyl parahydroxybenzoate | 0.015 g |
| (8) Purified water | 100 g |

The components (1) to (8) are formulated into an ointment for external skin application by a usual method for preparation of an ointment.

FORMULATION EXAMPLE 6 (Enema Formulation)

| | |
|---|---|
| (1) Active ingredient | 50 mg |
| (2) Macrogol 400 | 2 g |
| (3) Dipotassium phosphate | 141 mg |
| (4) Potassium dihydrogenphosphate | 44 mg |
| (5) Methyl parahydroxybenzoate | 20 mg |
| (6) Purified water | 50 g |

The active ingredient and methyl parahydroxybenzoate are added to Macrogol 400, followed by stirring to obtain a mixture, to which one obtained by adding dipotassium phosphate and potassium dihydrogenphosphate to the purified water is gradually added to prepare an enema formulation.

FORMULATION EXAMPLE 7 (Suppository)

| | |
|---|---|
| (1) Active ingredient | 50 mg |
| (2) Higher fatty acid glyceride | 1,650 mg |

The component (1) is dispersed or dissolved in (2), and packed and sealed in a plastic container having a size appropriate as a suppository, followed by cooling for solidification to prepare a suppository.

FORMULATION EXAMPLE 8 (Rectum Remaining Suppository, Controlled Release Suppository)

| | |
|---|---|
| (1) Active ingredient | 1 g |
| (2) Witepsol W35 | 19 g |

The component (1) is admixed with preliminarily heated and dissolved (2), and the admixture is packed and sealed in a plastic container having a size appropriate as a suppository, followed by cooling for solidification to prepare a suppository.

EXAMPLES

Test Example 1

As an ulcerative colitis model, trinitrobenzenesulfonic acid (TNB) is usually used, but as a drug effect evaluation system to accomplish the present invention, a rat sodium dextran sulfate (DSS) induced ulcerative colitis model was used. It has been well known that said model is considered as an experimental model similar to human ulcerative colitis from many viewpoints such as inhibision of weight gain, presence or absence of bloody stool, symptoms of e.g. anemia and formation of erosion at the large intestine, and no formation of lesion in the small intestine [FOLIA PHARMACOLOGICA JAPONICA vol. 105, p. 145–152(1995)]. A therapeutic effect of N-(2-ethylsulfonylamino-5-trifluoromethyl-3-pyridyl)cyclohexanecarboxamide sodium salt monohydrate (hereinafter referred to as compound 1) over the test system was examined.

The compound 1 was used as a drug formulation. The formulation composition (content per one vial) was as follows.

| | | |
|---|---|---|
| (a) | Compound 1 (as anhydride) | 100 mg |
| (b) | Mannitol (manufactured by KYOWA HAKKO KOGYO CO., LTD.) | 100 mg |
| (c) | Tris(hydroxymethyl)aminomethane (manufactured by JUNSEI CHEMICAL) | 21.6 mg |
| (d) | Hydrochloric acid (manufactured by SANKYO KAGAKU) | optimum amount |
| (e) | Sodium hydroxide (manufactured by Nippon Rika) | optimum amount |
| (f) | Distilled water | 10 ml |
| | pH 8.7 ± 0.5 | |

(1) Ulcerative Colitis Induction Method

A 3% aqueous solution of sodium dextran sulfate (DSS: manufactured by Wako Pure Chemical Industries, Ltd.) was put in a drinking bottle, and rats [Crj: CD(SD), male, Charles River Japan, 7 weeks old when subjected to the test] were made to drink the solution freely for 11 days to cause colitis. After eleven days, rats which satisfied selection standards (among rats which discharged bloody stool continuously for at least two days including the selection day, ones having a weight loss at the selection day of less than 20 g as compared with the weight on the previous day and having a hemoglobin concentration of at least 12 g/dl) were selected, and divided into groups (ten rats/group) so that there would be no difference in the average weight among groups.

With respect to a non-treated group and groups treated with the compound 1, the 3% aqueous solution was changed to a 1% DSS aqueous solution at the day of division, and the rats were made to drink the solution freely for 14 days. Further, to the rats in the groups treated with the compound 1, the compound 1 was perorally administered once a day for 14 days from the day of division by means of a peroral sonde (dosage: 10 ml/kg). To the rats in the non-treated group and a normal group, distilled water for injection (manufactured by Otsuka Pharmaceutical Co., Ltd.) alone was perorally administered similarly. Here, the normal group rats were made to drink distilled water for injection freely instead of the DSS aqueous solution from initiation of the test to the day of anatomy.

A 10 mg/ml aqueous solution of the compound 1 was prepared by using distilled water for injection (manufactured by Otsuka Pharmaceutical Co., Ltd.) and administered to the rats in a desired dosage.

(2) Evaluation Method

Length of Large Intestine and Erosion Area of Large Intestine Mucosa

Immediately after collection of blood, the large intestine (colon and rectum) was excised, and its length was measured by means of a ruler in a sufficiently relaxed state.

Immediately after the measurement, a fixing liquid was injected into the intestine, and the intestine was temporarily fixed for at least 1 hour in such a state that the lumen was approximately uniformly expanded. Then, the intestinal canal was dissected along the mesenterium adhered portion, and the intestine was completely fixed in an expanded state in a 10% neutral buffering formalin aqueous solution for at least one week. The intestine was washed with running water for about 5 minutes, and further washed with purified water three times, and then immersed in a 3% aqueous acetic acid solution for about 5 minutes as a pretreatment. Then, the intestine was immersed in a 1% Alcian blue (manufactured by Nacalai Tesque) (dissolved in a 3% aqueous acetic acid solution) and dyed for about 20 minutes, and then washed with a 3% aqueous acetic acid solution from 4 to 5 times until elution of Alcian blue disappeared. By this operation, the large intestine was dyed in blue with graduation, and the erosion portion was dyed in deep blue, and the area of the portion was analyzed by means of an image analyzer (general purpose image processing "WinROOF, Version 3.1", manufactured by MITANI CORPORATION) to obtain an erosion area.

The erosion suppression rate of the groups treated with the compound 1 was obtained taking the erosion area of the non-treated group as 100.

Erosion suppression rate (%)=[1−(average of erosion area of the groups treated with the compound 1/average of erosion area of the non-treated group)]×100

Histopathological examination: The large intestine, spleen, mesenterium and mesenteric lymph node, and femur bone marrow were fixed with a 10% neutral buffering formalin aqueous solution [prepared by using formalin (manufactured by Kishida Chemical Co., Ltd.), disodium hydrogen phosphate (manufactured by Wako Pure Chemical Industries, Ltd.) and sodium dihydrogen phosphate dihydrate (manufactured by Wako Pure Chemical Industries, Ltd.)], and a histopathological preparation having hematoxylin-eosin (manufactured by MERCK & CO., INC.) bichrome stain applied thereto in accordance with a conventional method was prepared and subjected to microscopic examination (by means of BX50, manufactured by OLYMPUS OPTICAL CO., LTD.).

(3) Results

Erosion area of large intestine: The compound 1 was perorally administered once a day over 2 weeks in a dose of 100, 10 or 1 mg/kg/day, and as a result, a suppression rate of 62, 56 or 45% in a large intestine erosion area as compared with the non-treated group was shown, and remarkable erosion suppression effect was confirmed (Table 1). Non erosion in large intestine was confirmed in the normal group.

TABLE 1

Effect on erosion area

| Dose of compound 1 (mg/kg/day) | Erosion suppression rate (%) | Significant test (non-treated group v.s. treated group) |
|---|---|---|
| 100 | 62 | P < 0.01 (Williams test) |
| 10 | 56 | P < 0.01 (Williams test) |
| 1 | 45 | P < 0.05 (Williams test) |

Length of large intestine: Further, it was also shown from studies on the length of the large intestine that the compound 1 decreases intestine wall hyperplasia which is an accessory lesion of the erosion, and decreases anemia as a result of melena due to the erosion.

Histopathological study: As a result of histopathological studies, a remarkable decrease of inflammation at the submucosa in the erosion formed region was confirmed in the groups treated with the compound 1. Further, it was confirmed that normal tissue reconstruction by regeneration of the mucosa took place, and the strength and function as the mucosal tissue tended to be restored.

Test Example 2

Therapeutic Effect on Trinitrobenzene Sulfonic Acid (TNBS) Induced Rat Crohn's Disease Model The therapeutic effect of the compound 1 on TNBS induced rat Crohn's disease model was studied by the following method.

(1) SD male rats (12 weeks old) were anesthetized with Nembutal and their abdomen was opened up, a TNBS solution (TNBS 160 mg/ml ethanol) was administered in 1 ml/kg in the colon located 10 cm below the ileocecum, and their abdomen was closed to prepare models, which were divided into a non-treated group and a group treated with the compound 1, each group consisting of 6 rats. No such a treatment was carried out for normal group rats. After preparation of the models, a drug formulation of the compound 1 of Test Example 1 diluted with distilled water was perorally administered to rats of the group treated with the compound 1 once a day for 7 days in a dosage of 10 mg/kg/day as calculated as anhydride of the compound 1. After completion of administration period, visual change, small intestine weight and mucosal myeloperoxidase activity in small intestine (mucosal MPO activity) were observed or measured. The visual change was evaluated by digitizing and compiling various changes. The ratio of the small intestine weight to the body weight was also calculated from the small intestine weight and the body weight. The results are shown in Table 2.

TABLE 2

Examination results

| | | Small intestine weight | | Ratio of small intestine to body weight | | Visual score | | Mucosal MPO activity | |
|---|---|---|---|---|---|---|---|---|---|
| Group | n | Mean | SD | Mean | SD | Mean | SD | Mean | SD |
| Normal group | 6 | 1.11 | 0.12 | 0.0030 | 0.0003 | 1.5 | 0.8 | 0.48 | 0.22 |
| Non-treated group | 6 | 2.18 | 0.45 ## | 0.0065 | 0.0009 ### | 7.8 | 0.8 ## | 8.93 | 3.71 ## |
| Treated group | 5 | 1.63 | 0.21 * | 0.0042 | 0.0005 *** | 4.2 | 0.4 ** | 0.89 | 0.05 ** |

Statistical Evaluation
Comparison between normal group and non-treated group #, ##, ###: p < 0.05, p < 0.01, p < 0.001
Comparison between non-treated group and treated group *, , *: p < 0.05, p <.0.01, p < 0.001

In the non-treated group, increase in values of the small intestine weight, the ratio of the small intestine to the body weight, the visual score and the mucosal MPO activity was confirmed, and an inflammatory reaction and tissue impairment in the small intestine were confirmed. It was shown that in the group treated with the compound 1, increase in such examination values was suppressed, and the inflammatory reaction and tissue impairment in the small intestine were decreased.

What is claimed is:

1. A method for preventing or treating a digestive system disease, comprising administering to a subject in need thereof an effective amount of a diaminotrifluoromethylpyridine compound or its salt, wherein said compound is represented by formula (I):

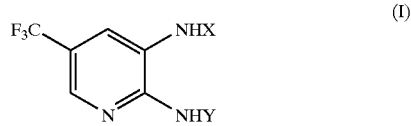

wherein
X is a —CW$^1$R$^1$ group, a —COCOR$^2$ group, a —CW$^1$NHCOR$^2$ group, a —C(=W$^1$)W$^2$R$^3$ group or a —CW$^1$N(R$^4$)R$^5$ group;
Y is an alkyl group, a —CW$^3$R$^6$ group, a —COCOR$^7$ group, a —NHCOR$^7$ group, a —C(=W$^3$)W$^4$R$^8$ group, a (NH)$_m$SO$_2$R$^9$ group, a —(NH)$_m$SO$_2$OR$^{10}$ group or a —(NH)$_m$SO$_2$N(R$^{11}$)R$^{12}$ group;
wherein each of R$^1$ R$^6$ and R$^9$, which are independent of one another, is a chain hydrocarbon group which may be substituted, a monocyclic hydrocarbon group which may be substituted, a polycyclic hydrocarbon group which may be substituted, a monocyclic heterocycle group which may be substituted or a polycyclic heterocycle group which may be substituted;
wherein each of R$^2$ and R$^7$, which are independent of each other, is an alkyl group which may be substituted, an alkoxy group which may be substituted, a phenyl group which may be substituted or a phenoxy group which may be substituted;
wherein each of R$^3$, R$^8$ and R$^{10}$, which are independent of one another, is an alkyl group which may be substituted, an alkenyl group which may be substituted, an alkynyl group which may be substituted, a cycloalkyl group which may be substituted, a phenyl group which may be substituted or a benzyl group which may be substituted;
wherein each of R$^4$, R$^5$, R$^{11}$ and R$^{12}$, which are independent of one another, is an alkyl group which may be substituted; each of W$^1$, W$^2$, W$^3$ and W$^4$ which are independent of one another, is an oxygen atom or a sulfur atom; and
wherein m is 0 or 1;
wherein said compound of formula (I) is not a compound where one of X and Y is a COCF$_2$X$^1$ group (wherein X$^1$ is a hydrogen atom, a halogen atom, an alkyl group or a haloalkyl group), and the other is a —COCF$_2$X$^2$ group (wherein X$^2$ is a hydrogen atom, a halogen atom, an alkyl group, a haloalkyl group or an alkylcarbonyl group), a —COOX$^3$ group (wherein X$^3$ is an alkyl group which may be substituted or a phenyl group which may be substituted) or a —COX$^4$ group (wherein X$^4$ an alkyl group, a haloalkyl group, an alkenyl group, an alkynyl group, a phenyl group which may be substituted, a furanyl group or a naphthyl group).

2. The method of claim 1, wherein
X is a —CW$^1$R$^1$ group or a —C(=W$^1$)W$^2$R$^3$ group and
Y is a —SO$_2$R$^9$ group.

3. The method of claim 1 wherein
X is a —CW$^1$R$_1$ group or a —C(=W$^1$)W$^2$R$^3$ group,
R$^1$ is an alkyl group which may be substituted, an alkenyl group which may be substituted, a cycloalkyl group which may be substituted, a cycloalkenyl group which may be substituted, a phenyl group which may be substituted, a tetrahydronaphthyl group which may be substituted, an indanyl group which may be substituted, a furanyl group which may be substituted or a thienyl group which may be substituted,
R$^3$ is an alkyl group which may be substituted,
Y is a —SO$_2$R$^9$ group, and
R$^9$ is an alkyl group which may be substituted, an alkenyl group which may be substituted, a cycloalkyl group which may be substituted, a cycloalkenyl group which may be substituted or a phenyl group which may be substituted.

4. The method of claim 1, wherein
X is a —CW$^1$R$^1$ group or a —C(=W$^1$)W$^2$R$^3$ group,
R$^1$ is an alkyl group, a haloalkyl group, an alkoxycarbonyl alkyl group, an alkenyl group, a haloalkenyl group, an alkenyl group substituted with a thienyl group, a cycloalkyl group, a cycloalkyl group substituted with a halogen atom, a phenyl group, a phenyl group substituted with a halogen atom, a phenyl group substituted with an alkyl group or a haloalkyl group, a phenyl group substituted with an alkoxy group or a haloalkoxy group, a tetrahydronaphthyl group, an indanyl group, a furanyl group or a thienyl group,
R$^3$ is an alkyl group or a haloalkyl group,
Y is a —SO$_2$R$^9$ group, and
R$^9$ is an alkyl group, a haloalkyl group, a phenyl group, a phenyl group substituted with a halogen atom, a phenyl group substituted with an alkyl group or a haloalkyl group, or a phenyl group substituted with an alkoxy group or a haloalkoxy group.

5. The method of claim 1, wherein
X is an alkoxycarbonyl alkylcarbonyl group, an alkenylcarbonyl group, an alkenylcarbonyl group substituted with a thienyl group, a cycloalkylcarbonyl group, an indanylcarbonyl group, a furancarbonyl group, a thiophenecarbonyl group, a tetrahydronaphthylcarbonyl group or a benzoyl group which may be substituted with a halogen atom or a halo alkyl group, and
Y is an alkylsulfonyl group.

6. The method of claim 1, wherein
X is a cycloalkylcarbonyl group, a furancarbonyl group or a benzoyl group which may be substituted with halogen, and
Y is an alkylsulfonyl group.

7. The method of claim 1, wherein
the diaminotrifluoromethylpyridine compound is N-(2-ethylsulfonylamino-5-trifluoromethyl-3-pyridyl)cyclohexane carboxamide, N-(2-methylsulfonylamino-5-trifluoromethy-3-pyridyl)-4-fluorobenzamide, N-(2-isopropylsulfonylamino-5-trifluoromethyl-3-pyridyl)-3-fluorobenzamide, N-(2-methylsulfonylamino-5-trifluoromethyl-3-pyridyl)-2-furancarboxamide or N-(2-isopropylsulfonylamino-5-trifluoromethyl-3-pyridyl)cyclopentanecarboxamide.

8. The method of claim 1 wherein the diaminotrifluoromethylpyridine compound is N-(2-ethylsulfonylamino-5-trifluoromethyl-3-pyridyl)cyclohexane carboxamide.

9. The method of claim 1 that is a method for preventing a digestive system disease.

10. The method of claim 1 that is a method for treating a digestive system disease.

11. The method of claim 1 that comprises treating a disease selected from the group consisting of ulcerative colitis (nonspecific idiopathic colitis), Crohn's disease (regional enteritis), large intestine Crohn's disease (granulomatous colitis or regional colitis), entero-Behcet's disease, infectious enteritis, ischemic enteritis, radioenteritis, drug enteritis, irritable bowel syndrome, digestive ulcer, gastric ulcer, duodenal ulcer, and gastritis.

12. The method of claim 1 comprising treating a subject with ulcerative colitis.

13. The method of claim 1 comprising treating a subject with Crohn's Disease.

14. The method of claim 1 further comprising administering at least one other drug, therapeutic agent or herbal remedy.

15. The method of claim 1 comprising administering an alkaline metal salt, an alkaline earth metal salt or an organic amine salt of said compound.

16. The method of claim 1 comprising administering said compound perorally.

17. The method of claim 16, wherein said compound is formulated in a manner to prolong its retention time in the digestive canal.

18. The method of claim 1 comprising administering said compound in the form of a tablet, capsule, powder, granule, troche, liquid, suspension, emulsion, ointment, suppository or syrup.

19. The method of claim 1 comprising administering said compound parenterally.

20. The method of claim 1 comprising administering said compound topically or by rectal administration.

21. The method of claim 1 comprising administering said compound via the respiratory airway or by inhalation.

22. The method of claim 1 comprising administering to a daily dose ranging from 0.1 mg to about 10 g of said diaminotrifluoromethylpyridine compound or its salt.

23. The method of claim 1 comprising administering a daily dose ranging from 1 mg to about 1 g of said diaminotrifluoromethylpyridine compound or its salt.

24. A method for decreasing intestinal wall erosion and/or hyperplasia in the large intestine comprising administering the compound of claim 1.

25. A method for inducing regeneration of the intestinal mucosa comprising administering the compound of claim 1.

26. A method for decreasing an inflammatory reaction or tissue impairment in the small intestine comprising administering the compound of claim 1.

* * * * *

UNITED STATES PATENT AND TRADEMARK OFFICE
CERTIFICATE OF CORRECTION

PATENT NO. : 6,653,333 B2
DATED : November 25, 2003
INVENTOR(S) : Yotsuya et al.

It is certified that error appears in the above-identified patent and that said Letters Patent is hereby corrected as shown below:

<u>Title page,</u>
Item [87], should read:
-- [87]  PCT Pub. No.:  WO01/56568
         PCT Pub. Date: Aug. 9, 2001 --

Signed and Sealed this

Twenty-third Day of March, 2004

JON W. DUDAS
*Acting Director of the United States Patent and Trademark Office*